United States Patent
Muzik et al.

(10) Patent No.: US 12,009,009 B2
(45) Date of Patent: Jun. 11, 2024

(54) SYSTEMS AND METHOD OF PROVIDING HEALTH INFORMATION THROUGH USE OF A PERSON'S VOICE

(71) Applicant: Sonaphi, LLC, Incline Village, NV (US)

(72) Inventors: Brandon Muzik, San Rafael, CA (US); Mark Hinds, Incline Village, NV (US); Robert D. Fish, Irvine, CA (US)

(73) Assignee: Sonaphi LLC, Incline Village, NV (US)

( * ) Notice: Subject to any disclaimer, the term of this patent is extended or adjusted under 35 U.S.C. 154(b) by 0 days.

(21) Appl. No.: 18/120,382

(22) Filed: Mar. 11, 2023

(65) Prior Publication Data

US 2023/0290372 A1    Sep. 14, 2023

Related U.S. Application Data

(60) Provisional application No. 63/319,368, filed on Mar. 13, 2022.

(51) Int. Cl.
| | |
|---|---|
| G10L 25/66 | (2013.01) |
| G10L 15/30 | (2013.01) |
| G16H 20/00 | (2018.01) |
| G16H 50/30 | (2018.01) |

(52) U.S. Cl.
CPC .............. *G10L 25/66* (2013.01); *G10L 15/30* (2013.01); *G16H 20/00* (2018.01); *G16H 50/30* (2018.01)

(58) Field of Classification Search
CPC ........... A61B 5/00; G10L 25/66; G10L 15/30; G16H 20/00; G16H 50/30
See application file for complete search history.

(56) References Cited

U.S. PATENT DOCUMENTS

| | | |
|---|---|---|
| 9,070,357 B1 | 6/2015 | Kennedy et al. |
| 9,198,613 B2 | 12/2015 | Oh et al. |
| 10,152,988 B2 | 12/2018 | Kim et al. |
| 10,478,111 B2 | 11/2019 | Knoth et al. |
| 10,896,765 B2 | 1/2021 | Kim et al. |
| 10,932,714 B2 | 3/2021 | Sanderson et al. |
| 11,004,461 B2 | 5/2021 | Howard |

(Continued)

FOREIGN PATENT DOCUMENTS

| | | |
|---|---|---|
| JP | 2020522028 | 7/2020 |
| KR | 1020200052175 A | 5/2020 |
| WO | WO2018204935 | 11/2018 |

OTHER PUBLICATIONS

International Search Report and Written Opinion in corresponding International Application No. PCT/US2023/015042, dated Jul. 3, 2023, 8 pages.

*Primary Examiner* — Huyen X Vo
(74) *Attorney, Agent, or Firm* — Fish IP Law, LLP

(57) ABSTRACT

A system that can capture a user's voice sample and, based on a comparison with other voice samples stored in a database, determine the existence of one or more musculoskeletal conditions within the user's body. The analysis of the voice sample include determining various voice characteristics of the sample against those that are in the database-stored samples to determine matches with conditions and their associated severities. The results are presented via an application that can present location and severity on a 3D avatar model.

13 Claims, 7 Drawing Sheets

(56) References Cited

U.S. PATENT DOCUMENTS

| | | |
|---|---|---|
| 2006/0036440 A1 | 2/2006 | Kunkel |
| 2012/0116186 A1 | 5/2012 | Shrivastav et al. |
| 2012/0220899 A1 | 8/2012 | Oh et al. |
| 2013/0095459 A1 | 4/2013 | Tran |
| 2017/0112418 A1* | 4/2017 | Comeau .................. A61B 5/318 |
| 2017/0206795 A1 | 7/2017 | Kaleal, III |
| 2023/0054890 A1* | 2/2023 | Raj ......................... G16H 10/60 |

* cited by examiner

SYSTEMS AND METHOD OF PROVIDING HEALTH INFORMATION THROUGH USE OF A PERSON'S VOICE

This application claims priority to U.S. provisional application 63/319,368, filed Mar. 13, 2022. U.S. provisional application 63/319,368 and all other extrinsic references contained herein are incorporated by reference in their entirety.

FIELD OF THE INVENTION

The field of the invention is identifying physiological issues via voice analysis.

BACKGROUND

Typically, people find health information by considering their own body's aches and pains, and/or by reaching out to a medical professional, who will assess both the objective signs and the subjective symptoms. Unfortunately, many people have inadequate backgrounds in anatomy and physiology to make proper self-assessments, and medical professionals are often unavailable, or can only be accessed at high cost, and usually only one client, one test at a time.

Even where medical professionals are available, and can be accessed along with their various diagnostic equipment and therapeutic modalities, they are often focused on acute problems, rather than underling root causes. Even where proper diagnoses are made, there can also be problems with assessing progress and effectiveness of any treatments. Progress can be subtle, stretching out over weeks, months, or even years.

Non-traditional health professionals might tend to be more focused on root causes, but they might similarly be unavailable, or not have the needed knowledge or tools. One tool that could be made available to substantially everyone, is self-assessment of health information through voice. Research scientist Sharry Edwards has pioneered work in that arena for at least three decades, but her work has focused more on education, and has not matured into a readily available product. There have been a handful of other players in the field. For example, Beyond Verbal uses vocal patterns to identify emotional health parameters, and Sonde uses vocal patterns to identify mental health parameters. U.S. Pat. No. 10,932,714 to Sanderson et al. teaches identifying useful biometric signals from a person's voice, and subjecting the person's body to compensating electronic signals.

U.S. Pat. No. 10,932,714 and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

One of the difficulties with all of the known voice analysis technologies is that they are not focused on musculoskeletal systems of the body, and are therefore difficult to translate into recommendations for corrective exercises that a person can implement on their own, for example, through stretching, foam rolling, stabilization, corrective exercises, strength training. For example, gym members might not be able to afford a personal trainer, and therefore might have insufficient understanding of exercise technique, specific muscle and/or muscle groups that need to be target, and ways of targeting those. This can certainly be the case with child athletes, and even all the way through to professional athletes.

What is needed is a voice analysis technology that can be implemented on cell phones or other commonly available electronics, which associates voice patterns with problematic musculoskeletal issues, and provide even unsophisticated users with exercises and other recommendations for corrective exercises, which they can implement on their own. What is also needed is for such technology to be sufficiently sensitive and accurate, so that users can ascertain their progress by easily re-testing after following the recommendation(s).

SUMMARY OF THE INVENTION

The inventive subject matter provides apparatus, systems, and methods in which computer analysis of a person's voice is used to provide the person with health information.

A client device captures a voice sample for a user, which is transmitted to a server that can determine one or more voice characteristics from the voice sample. The voice characteristics can be then matched with voice characteristics of voice samples stored in a database that are associated with one or more conditions. Additionally, the server can determine a severity for any associated conditions.

The results of the analysis are returned to the client device which can present them in the form of markers on parts of a 3D avatar. The user client device can present additional information about the markers, including a greater description of the condition and suggested exercises or other treatment.

Various objects, features, aspects and advantages of the inventive subject matter will become more apparent from the following detailed description of preferred embodiments, along with the accompanying drawing figures in which like numerals represent like components.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

DETAILED DESCRIPTION

Figure 1:
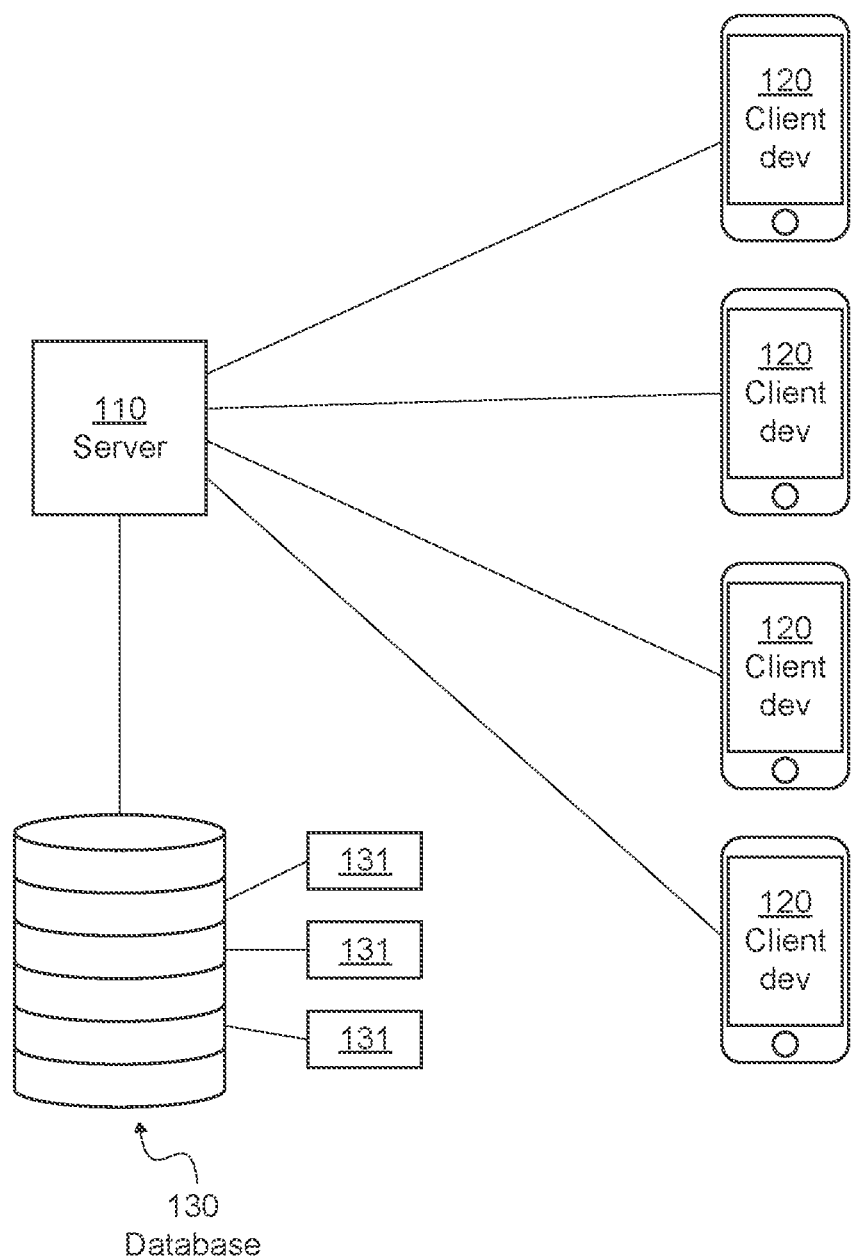
FIG. 1 is a diagrammatic overview of a system according to embodiments of the inventive subject matter.

Throughout the following discussion, numerous references will be made regarding servers, services, interfaces, engines, modules, clients, peers, portals, platforms, or other systems formed from computing devices. It should be appreciated that the use of such terms, is deemed to represent one or more computing devices having at least one processor (e.g., ASIC, FPGA, DSP, x86, ARM, ColdFire, GPU, multi-core processors, etc.) programmed to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In preferred embodiments, a cell phone, tablet, or other ordinary consumer electronic device is used to make a recording of the person's voice. The recording is sent to a receiving portal for processing, which involves using the voice recording to identify musculoskeletal biomarkers and corresponding intensities. That information is then returned to the sending device, which displays the biomarkers in corresponding body locations of an avatar. Avatars are preferably 3D representations of a person, such that a viewer can visualize front, side, and back views of the avatar.

Biomarkers are used to represent particular muscles, muscle groups, or bones, and are preferably shown using colored markers, with different colors representing different intensities.

Biomarkers and intensities are also depicted in list form, associated with corrective exercises, and possibly other nutrition or other recommendations.

The voice recording is preferably analyzed through comparison with previously collected correlations between collected voice samples and multiple musculoskeletal biomarkers of other persons. In some embodiments the previously collected correlations can be derived from amplitude frequency sweeps of the collected voice samples, and Verification can be accomplished by applying a Tens unit or other electrical stimulation to a particular muscle or a muscle group to verify data in the set of correlations. Verification can additionally or alternatively be accomplished using exercise or manual stimulation of a particular muscle or a muscle group.

FIG. 1 is a diagrammatic overview of a system 100, according to embodiments of the inventive subject matter.

System 100 can include a server or other computing device 110 that can perform the server-side processes discussed herein. The server 110 can be one or more computing devices at one or more locations that include at least one processor and at least one non-transitory computer-readable storage medium (e.g., hard drives, RAM, etc.) that can store data and executable instructions as discussed herein.

Also seen in FIG. 1 is a plurality of client devices 120. The devices 120 are computing devices that include at least one processor, at least one data exchange module (e.g., Wi-Fi, cellular, ethernet, etc.), a memory (e.g., hard drive, RAM, ROM, etc.) to store program instructions and relevant data, and an input/output ("I/O") interface that includes an audio sensor (e.g., a microphone) and optionally other I/O interfaces as well (e.g., monitor with mouse and keyboard, touch screen, stylus etc.). Examples of suitable client devices 120 can include, but are not limited to, mobile phones, tablets, desktop computers, laptop computers, game consoles, in-car computers, etc.

To access the functions discussed herein, a user can download an application to the client device 120, such as from an App Store. The application can be used by the user to interact with the system 100 include entering information and receiving information visually and aurally (e.g., via displays of an avatar with associated biomarkers and locations, presenting information about a condition, etc.). In embodiments, the functions could be accessed via a web portal accessible via an internet browser.

The server 110 can include or be in communication with a database 130 that includes a collection of voice samples 131. The voice samples 131 can include voice samples of the user reciting certain words or phrases and also/alternatively can include a collection of voice samples from other users reciting these words or phrases. The voice samples stored in database 130 are of specific words, phrases or sentences that a user will later be prompted to recite when using the application.

The voice samples 131 include a plurality of voice characteristics. The voice characteristics are characteristics of the sonic qualities of the voice sample 131, excluding linguistic data. As used herein, "linguistic data" comprises any information that requires knowledge of language to decipher and/or understand, such as English, Spanish, Mandarin Chinese, etc. In other words, certain words could be used to elicit certain audio cues from the speaker but not the meaning of the words themselves. Examples of measurable voice characteristics can include frequency, pitch, amplitude, volume, voice fluidity, and tone.

The voice samples 131 can correspond to voice samples taken for the user and/or for other users when the user/other users were healthy (i.e., not suffering from any of the conditions that can be determined by the system). Thus, the voice characteristics of the voice samples will reflect those of a healthy user.

In embodiments of the inventive subject matter, the voice samples 131 can include voice samples taken for the user and/or other users when the user/users have been diagnosed or otherwise determined to be suffering from a particular condition. Thus, in these embodiments, the voice characteristics reflect those changes in the characteristics resulting from a particular condition.

The words, phrases or sentences used in both the stored voice samples 131 and that the user are asked to recite are selected because they contain a sufficiently large amount of characteristics when spoken that can then be analyzed and broken down.

In embodiments of the inventive subject matter the database 130 also stores a plurality of conditions that includes one or more voice characteristics that are known to be affected by the condition. As will be discussed below in further detail, the conditions can include a condition signature (in some embodiments). In embodiments, the stored conditions can include thresholds for the voice characteristics that need to be met in order for the stored condition to be returned as a possible identified condition. Along with the condition, the database 130 can also store a scale or degree of severity for each condition.

The conditions in the database 130 also include information associated with one or more musculoskeletal biomarkers. This musculoskeletal biomarkers can include the name of the condition as well as the location on the body that will be displayed over an avatar by the application installed on client device 120.

In embodiments of the inventive subject matter, the conditions stored in the database 130 can be conditions associated with the categories of Digestion, Hydration, Sleep, Stress, Energy. Other suitable categories can include muscular, structural, flexibility, strength, etc.

As discussed elsewhere herein, the system 100 can build the contents of the database by collecting voice samples from a cohort of persons and developing a set of correlations between the collected voice samples and the various conditions (e.g., the musculoskeletal biomarkers). This can include a manual input of the known conditions to help the system 100 (e.g., via server 110 and/or other computing devices) develop the correlations between the voice samples and the conditions themselves. These voice samples can, as discussed herein, be used as the basis of the comparison with a user-provided voice sample for the purposes of determining the applicable conditions/biomarkers.

Figure 2:
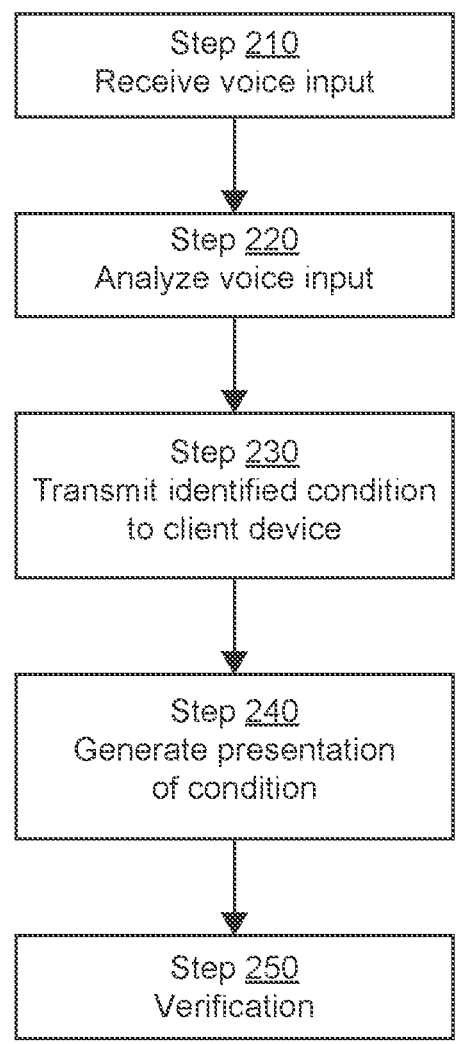
FIG. 2 a flowchart of a process whereby a user can obtain information about their body condition, according to embodiments of the inventive subject matter.

FIG. 2 is a flowchart of a process whereby a user can obtain information about their body condition, according to embodiments of the inventive subject matter.

At step 210, a client device 120 receives, via an audio sensor such as a microphone, voice input from a user. The system 100, via client device 120, can receive sufficient information to carry out its processes solely by the use of the client device 120's audio capture capabilities (e.g., via on-board microphone or via an attached microphone). This means the system does not require any additional external attachments such as specialized biological or physiological sensors.

In embodiments of the inventive subject matter, the client device 120 can present a prompt of one or more words, phrases or sentences that the user the has to repeat. When the user repeats these sentences, the client device 120 captures the recitation of the prompts by the user via the audio sensor.

At step 220, the system 100 analyzes one or more characteristics of the obtained voice input. In embodiments such as the one discussed herein, some or all of the analysis can be performed by the server 110. In these embodiments, the voice input is transmitted from the client device 120 to the server 110, which the performs the analysis. In some embodiments, the analysis can be performed by the client device 120. In these embodiments, the client device 120 must have sufficient processing power and sufficient memory to store the data it needs to carry out the processes discussed herein.

Figure 3:
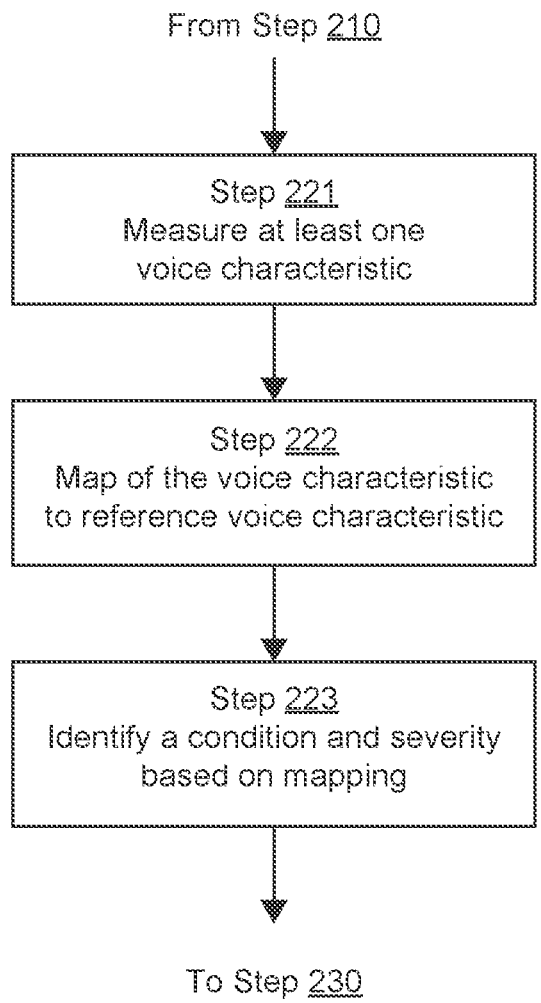
FIG. 3 is a flowchart showing the detailed steps that make up step 220 of FIG. 2.

The analysis of step 220 is broken down into detail in FIG. 3, as follows:

At step 221, the server 110 measures at least one voice characteristic from the voice input.

At step 222, the server 110 maps the at least one voice characteristic from the voice input to at least one reference voice characteristic from one or more reference voice samples 131 stored in database 130.

At step 223, the server 110 identifies a condition and a severity based on the mapped at least one voice characteristic from the voice input to the at least one reference voice characteristic of the one or more reference voice samples 131.

The server 110 can identify an applicable condition among the plurality of conditions in several ways.

In embodiments of the inventive subject matter, the server 110 can first determine a variance for each of the one or more voice characteristics from the voice input from the corresponding mapped voice characteristic of the voice sample(s) 131. In these embodiments, the voice characteristics of the stored voice samples 131 can be considered a baseline against which the voice characteristics of the voice input are measured because the voice characteristics The baseline values are the values of the voice characteristics that correspond to a person that is not suffering from any of the identifiable conditions.

In these embodiments, the server 110 then compares the variance of each voice characteristics against one or more condition signatures stored in the database 130. A condition signature is considered to be a collection of variances for a plurality of voice characteristics that represents the existence of a condition within a person. The server 110 then identifies one or more conditions based on the comparison of the variances in the voice sample against the condition signatures. An identified condition can be based on one or more of the variances matching one or more of the variances in the corresponding condition signature (e.g., one or more variance amounts match one or more threshold variance amounts for the corresponding voice characteristics for a particular condition signature). It is contemplated that the threshold for an identified condition may be that all of the variances in the voice characteristics from the voice input must match or exceed the variances in the condition signature for the condition to be returned.

For example, if a condition signature associated with a particular condition has variances of a certain amount in pitch, frequency and tone, the server 110 will match the condition associated with the condition signature if the variances for pitch, frequency and tone in the voice characteristics of the supplied voice sample meet or exceed the variances from the condition signature.

In other embodiments, the server 110 can calculate a confidence score based on the number of measured variances that exceed the variances in the condition signature (e.g., a percentage based on how many variances exceed the condition signature variance amounts). In these embodiments, the server returns a confidence associated with the condition to the device 120 as discussed further below.

For example, if a condition signature associated with a particular condition has variances of a certain amount in pitch, frequency and tone, but the variances of the voice characteristics only meet or exceed pitch and frequency but not tone, the server 110 can return this condition as a possible condition with a degree of confidence (in this simplified example, 66%).

In the above embodiments, the server 110 can determine the severity of a condition by determining the magnitude by which the variance of the voice characteristics of the voice sample provided by the user exceeds the thresholds of the variance of the corresponding voice characteristics of the condition signature.

As noted above, in embodiments of the inventive subject matter the voice samples 131 stored by the database 130 can include voice samples from users that have a known condition. Thus, in these embodiments, the voice samples 131 have the voice characteristics that reflect having that condition. Additionally, voice samples 131 can include a plurality of samples for a plurality of conditions of varying severity. As such, the database 130 stores voice samples 131 that reflect various levels of severity for a given condition.

In these embodiments, the server 110 can determine the existence and severity of a condition by matching the voice sample received from the user with one or more of the voice samples 131 stored in the database 130.

The server 110 can perform this matching on the basis of the voice characteristics of the provided voice sample against the voice characteristics of the voice samples 131 in the database 130. The server 110 can perform this matching via cluster recognition algorithms or other statistical matching techniques.

Because a well-populated database 130 will include many voice samples 131 for the varying severity of any given condition, the server 110 will likely return many potential voice samples 131 for a particular condition that will match (and potentially, identify more than one condition if the voice characteristics are sufficiently close) which provides greater confidence of the matched condition as well as the ascertained severity.

Based on these matches, the server 110 can determine a confidence score according to the distribution of the matches.

One suitable method of extracting information from a voice sample and analyzing it for the purposes of identifying a condition in the user can be found in Applicant's own issued U.S. Pat. No. 10,932,714, incorporated herein by reference.

The severity of a particular condition/musculoskeletal biomarker can be considered to be an "intensity of incoherence", which refers to a difference between the actual condition of the user's body part or section and a "normal" or "healthy" condition.

At step 230, the server 110 transmits back information to the client device 120 about the identified condition. The information includes data an identification of the condition itself (e.g., the clinical name, a common name (if applicable), the severity, the location of the body, and one or more remedial measures.

At step 240, the client device 120 receives the information and presents the information to the user.

The system 100 can further verify the information presented to the user based on an attempt to treat the condition returned at step 240. Thus, at step 250, the client device 120 can ask the user to provide their feedback after an attempt to treat the condition has been carried out. The attempts at treatment can include applying a Tens unit or other electrical stimulation to the affected area (if it is a muscular condition, for example). The attempt at treatment can include exercises of a particular type and/or manual stimulation of a particular muscle or muscle group.

The feedback can be in the form of a simple yes or no question such as "Did the treatment alleviate the condition?" It can include an ability for the user to provide a degree of improvement if at all (e.g., "On a scale of 1-10, how much has it improved?")

This verification is then passed to the server 110 to further train the system such that the accuracy of the analysis can be improved.

Figure 4:
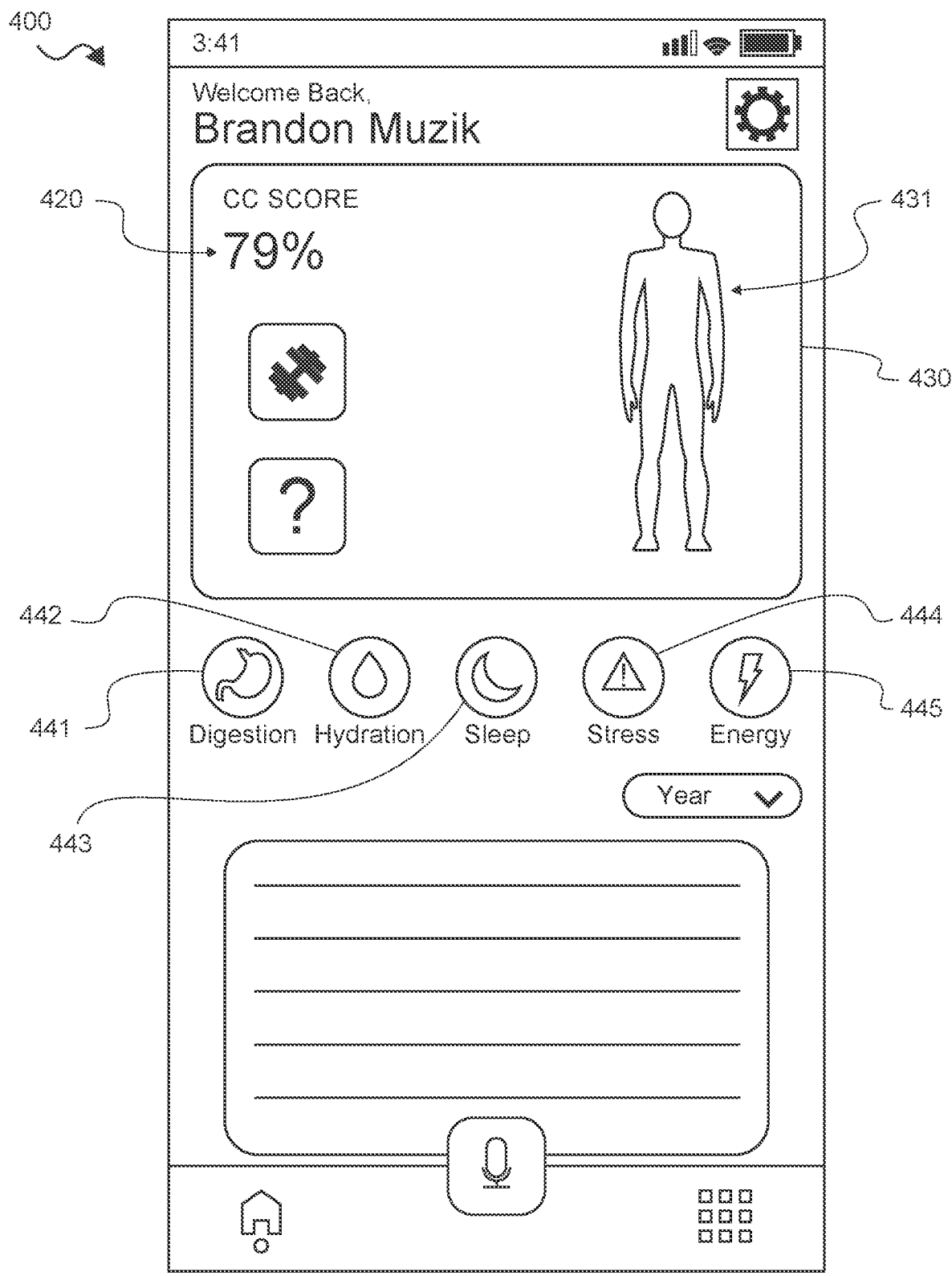
FIG. 4 is an example of a screen shot of a dashboard of a mobile device application operating on client device.

FIG. 4 is an example of a screen shot 400 of a dashboard of a mobile device application operating on client device 120. The dashboard shows an avatar display box 410, having a "Cellular Coherence Score" 420 in the upper left corner, and a generic 2D avatar representation 431 that serves as a link to a 3D muscle avatar specific to the user that will be shown further below. Beneath the avatar display box 430 are icons 441-445 serving as links to 5 different categories of health information that can be analyzed: Digestion, Hydration, Sleep, Stress, and Energy. The Cellular Coherence Score can be, in embodiments, an aggregation of the conditions and their severity as a deviation from a fully-healthy individual.

Figure 5:
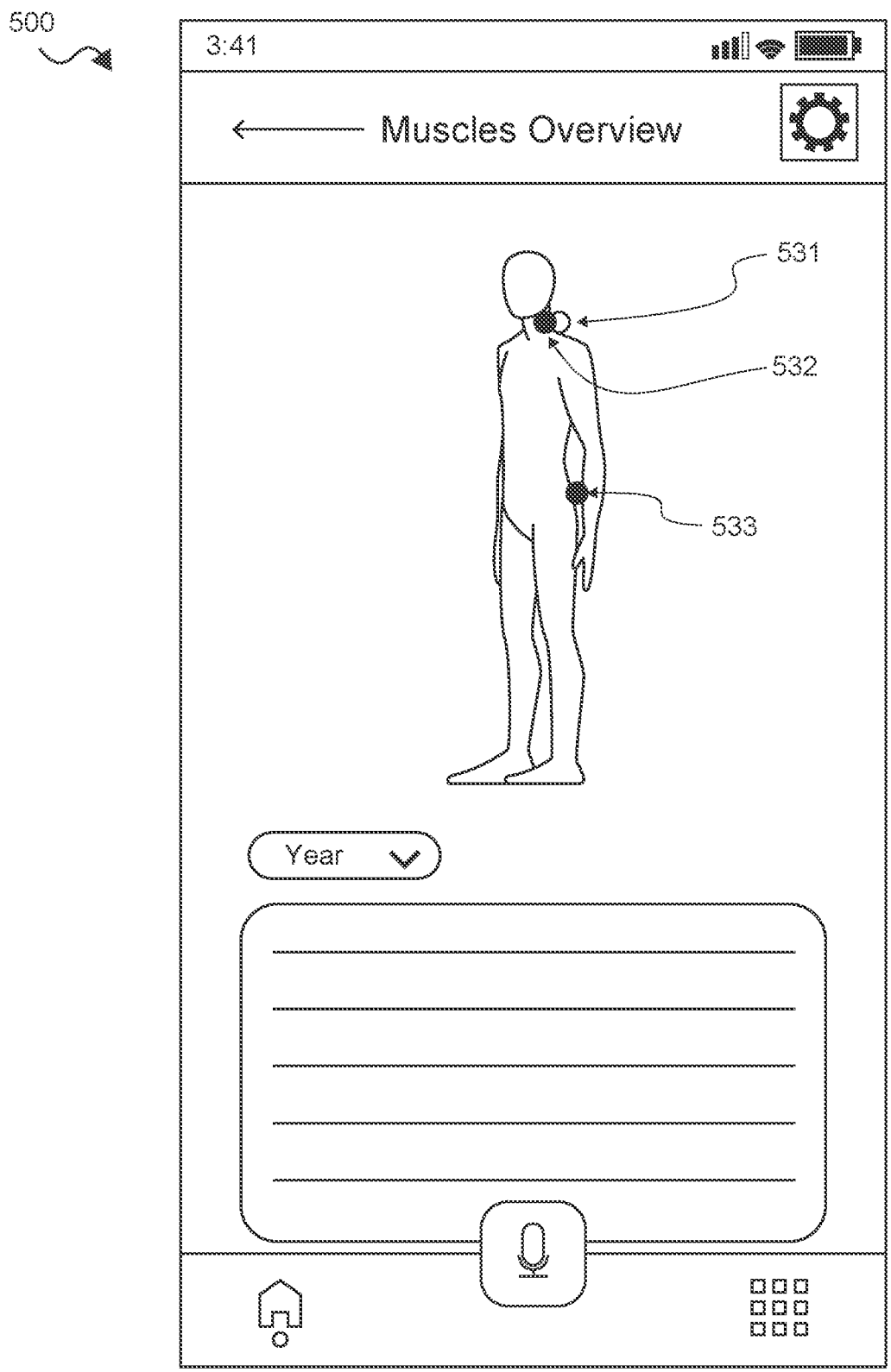
FIG. 5 is a representation of the landing page triggered by a user clicking on the 2D avatar.

FIG. 5 is a representation of the landing page 500 triggered by a user clicking on the 2D avatar 431. Here, the 3D avatar 520 has visually-distinct markers 531, 532, 533 that highlight particular musculoskeletal biomarkers that have been determined by voice analysis to have the highest intensity of incoherence. The 3D avatar is rotatable so that the user can see highlighted musculoskeletal biomarkers on the front, sides and back of the avatar.

Figure 6:
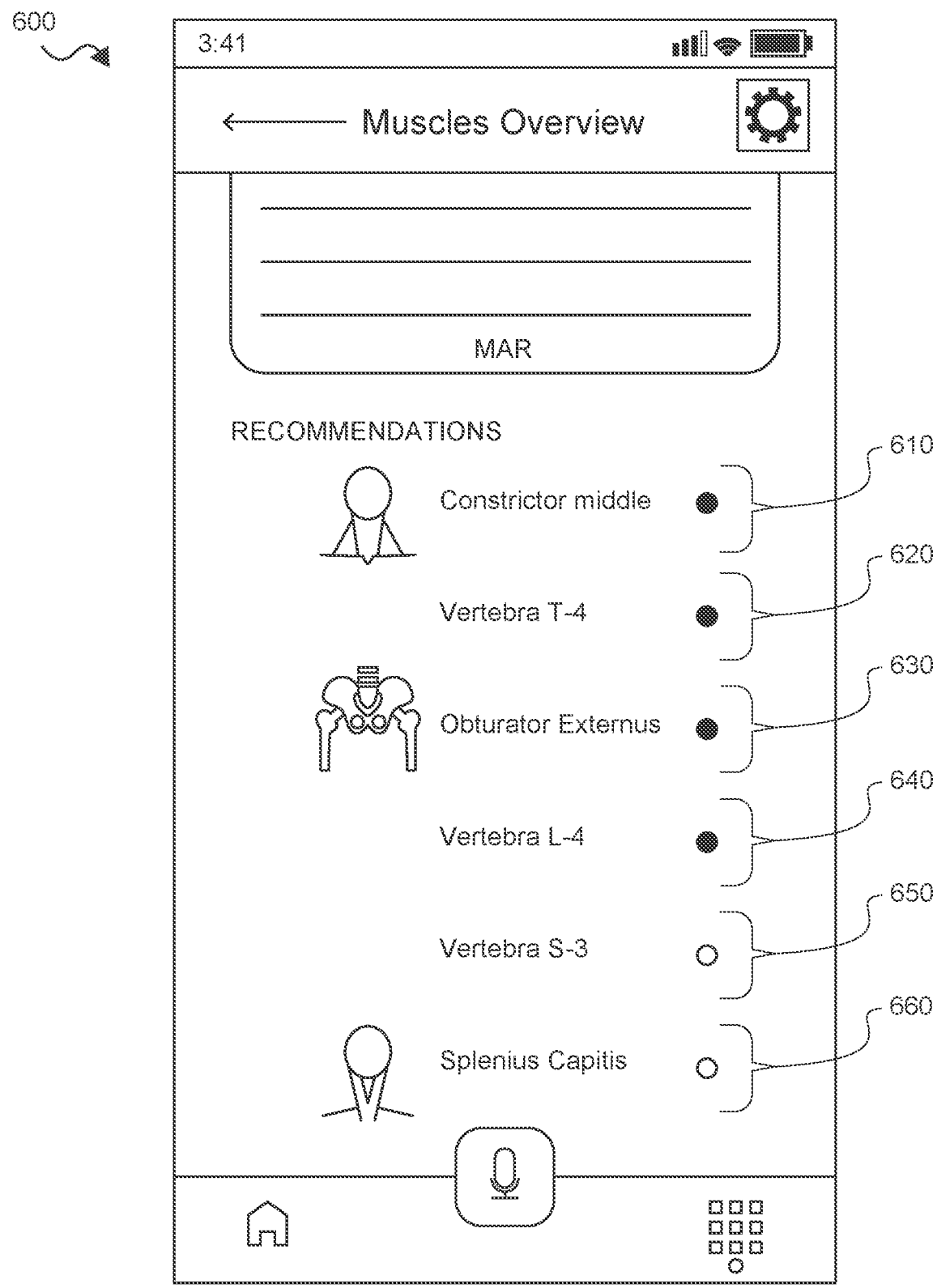
FIG. 6 is a representation of a page of the mobile device application that provides additional details regarding the condition.

FIG. 6 is a representation of a page of the mobile device application that provides additional detail. Here, a listing depicts small anatomic representations 610-660 of regions identified by the highlighted musculoskeletal biomarkers in FIG. 5, as well as the names of the corresponding muscles or other anatomical features, and visually-distinct dots depicting levels of intensities. The list is sorted by highest to lowest levels of intensity. In the example of FIG. 6, there are four filled-in dots showing relatively higher levels of intensity, and two hollow dots showing relatively lower levels of intensity. This is for the purposes of illustration—the dots of FIGS. 5-6 can have different colors (e.g., red for higher intensity, green for lower intensity) or other visually-distinct features that allow a user to quickly see the areas of higher versus lower intensity.

Figure 7:
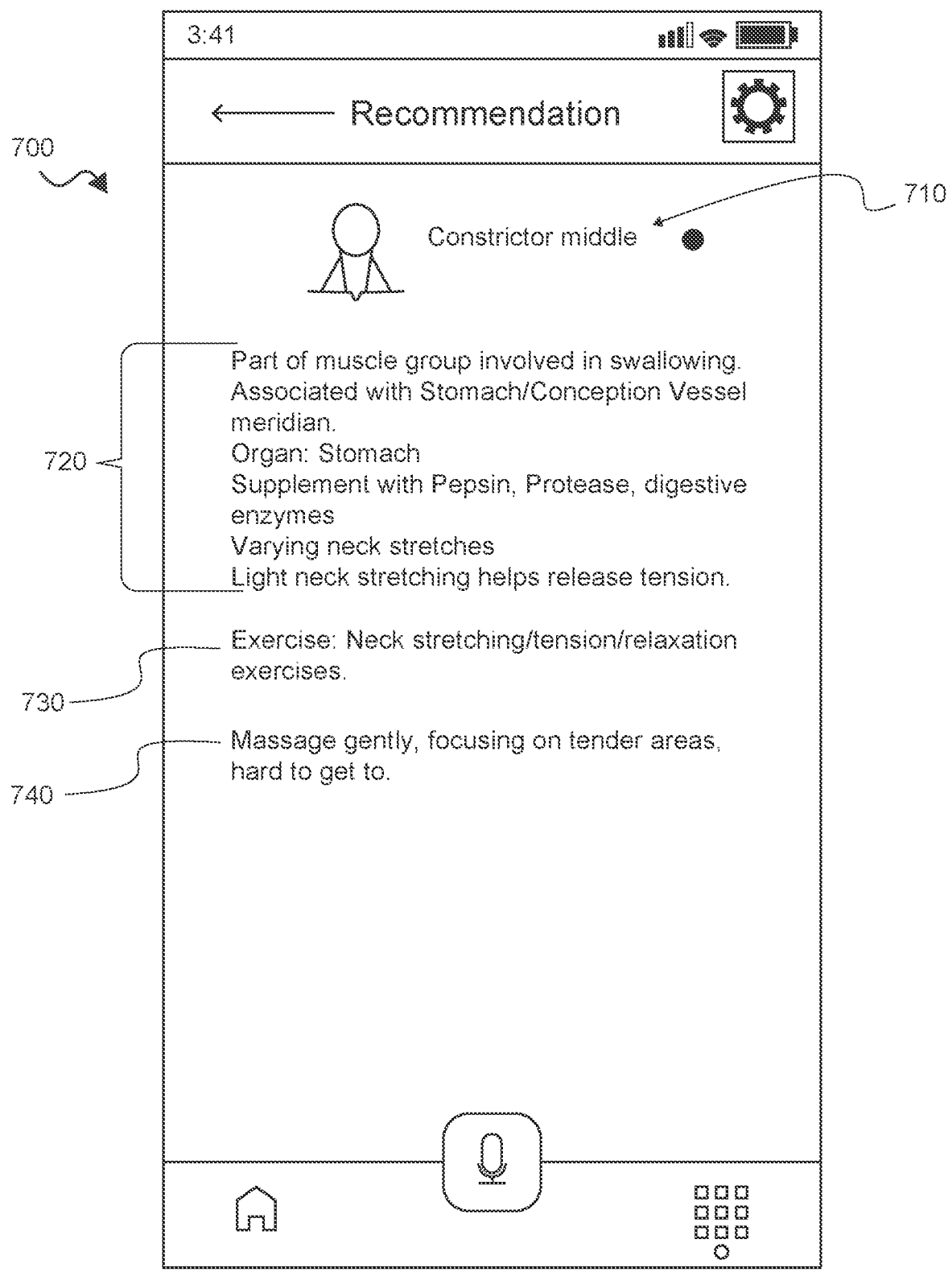
FIG. 7 is a representation of a screen from the same a mobile device application that provides additional information with respect to a selected one of the highlighted musculoskeletal biomarkers selected from FIG. 6.

FIG. 7 is a representation of a screen 700 from the same a mobile device application that provides additional information with respect to a selected one of the highlighted musculoskeletal biomarkers 710 (corresponding to item 610) selected from FIG. 6. Thus, the app on client device 120 is programmed to display this information upon a user clicking or otherwise selecting one of the biomarkers from FIG. 6. The additional information includes additional anatomical and physiological information 720, as well as recommended exercises 730 and additional potential treatment information or other suggestions 740.

Various objects, features, aspects and advantages of the present invention will become more apparent from the following detailed description of preferred embodiments of the invention.

Thus, specific embodiments and applications of methods have been disclosed, for providing health information through use of a person's voice. It should be apparent, however, to those skilled in the art that many more modifications besides those already described are possible without departing from the inventive concepts herein. The inventive subject matter, therefore, is not to be restricted except in the spirit of the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A method of providing health information through use of a person's voice, comprising:
    capturing a voice recording from the person;
    using at least one processor to:
        retrieve at least one voice characteristic from the voice recording;
        map the at least one voice characteristic to at least a first musculoskeletal biomarker among a plurality of musculoskeletal biomarkers;
        identify the at least a first musculoskeletal biomarker with a corresponding first intensity based on the mapping;
        using an avatar to display a location of the first biomarker;
        visually depict an indicator of the first intensity;
        present at least one recommendations depending on the location of the first biomarker and the first intensity; and
        wherein the different recommendations include at least one of a corrective exercise and a corrective therapy.

2. The method of claim 1, further comprising using a cell phone or other mobile consumer device to capture the voice recording, without requiring any extraneous attachment.

3. The method of claim 1, further comprising collecting voice samples from a cohort of persons, and developing a set of correlations between the collected voice samples and multiple musculoskeletal biomarkers of the different persons, and comparing the voice recording to data in the set of correlations.

4. The method of claim 3, further comprising adding to the set of correlations, first intensity information derived from amplitude frequency sweeps of the collected voice samples.

5. The method of claim 3, further comprising applying a Tens unit or other electrical stimulation to a particular muscle or a muscle group to verify data in the set of correlations.

6. The method of claim 3, further comprising using manual stimulation of a particular muscle or a muscle group to verify data in the set of correlations.

7. The method of claim 1, wherein the avatar comprises a 3D representation of a person, such that a viewer can visualize front, side, and back views of the avatar.

8. The method of claim 1, wherein the indicator uses color coding to designate the first intensity.

9. The method of claim 1, further comprising depicting the indicator both on the avatar, and in a listing that correlates the indicator with an associated one of the different recommendations.

10. The method of claim 9, wherein the listing further correlates the indicator with an anatomical representation of a body located near the indicator on the avatar.

11. The method of claim 9, further comprising using the voice recording to identify at least a second musculoskeletal biomarker with a corresponding second intensity; and using an avatar to display a location of the second biomarker; and wherein the listing ranks the first and second musculoskeletal biomarkers with respect to their corresponding first and second intensities.

12. The method of claim 1, wherein the at least processor uses artificial intelligence to process the voice recording to identify at least the first musculoskeletal biomarker with the first intensity.

13. The method of claim 1, further comprising providing a software app through an app store, which collects the voice recording, and transmits the voice recording to a receiving portal, receives data from a delivery portal, and presents the received data to a user in an interface that include the avatar.

* * * * *